United States Patent [19]

Hamlin, Jr.

[11] Patent Number: 4,986,875
[45] Date of Patent: Jan. 22, 1991

[54] TOOL FOR REMOVING TABS AND BRACKETS FROM WINDSHIELDS

[76] Inventor: Virgil E. Hamlin, Jr., 5740 Patton Way, Bakersfield, Calif. 93308

[21] Appl. No.: 440,691

[22] Filed: Nov. 24, 1989

[51] Int. Cl.$^5$ ............................................. B32B 31/18
[52] U.S. Cl. ..................................... 156/584; 30/140; 30/169; 156/344; 219/227; 219/230
[58] Field of Search .................. 30/140, 169; 156/344, 156/584; 219/227, 229, 230

[56] References Cited

U.S. PATENT DOCUMENTS

| | | | |
|---|---|---|---|
| 2,139,554 | 12/1938 | Martin | 219/229 |
| 2,417,943 | 3/1947 | Muller | 219/229 |
| 2,952,763 | 9/1960 | Gustafsson | 219/229 X |
| 4,690,724 | 9/1987 | Outlaw | 156/584 |

Primary Examiner—Robert A. Dawson

[57] ABSTRACT

A tool for removing mirror brackets and tabs therefor from windshields of automobiles and the like. The tool includes an electrical heating apparatus which permits single-handed operation. The tool operates quickly and efficiently without damaging windshields or other glass components.

13 Claims, 1 Drawing Sheet

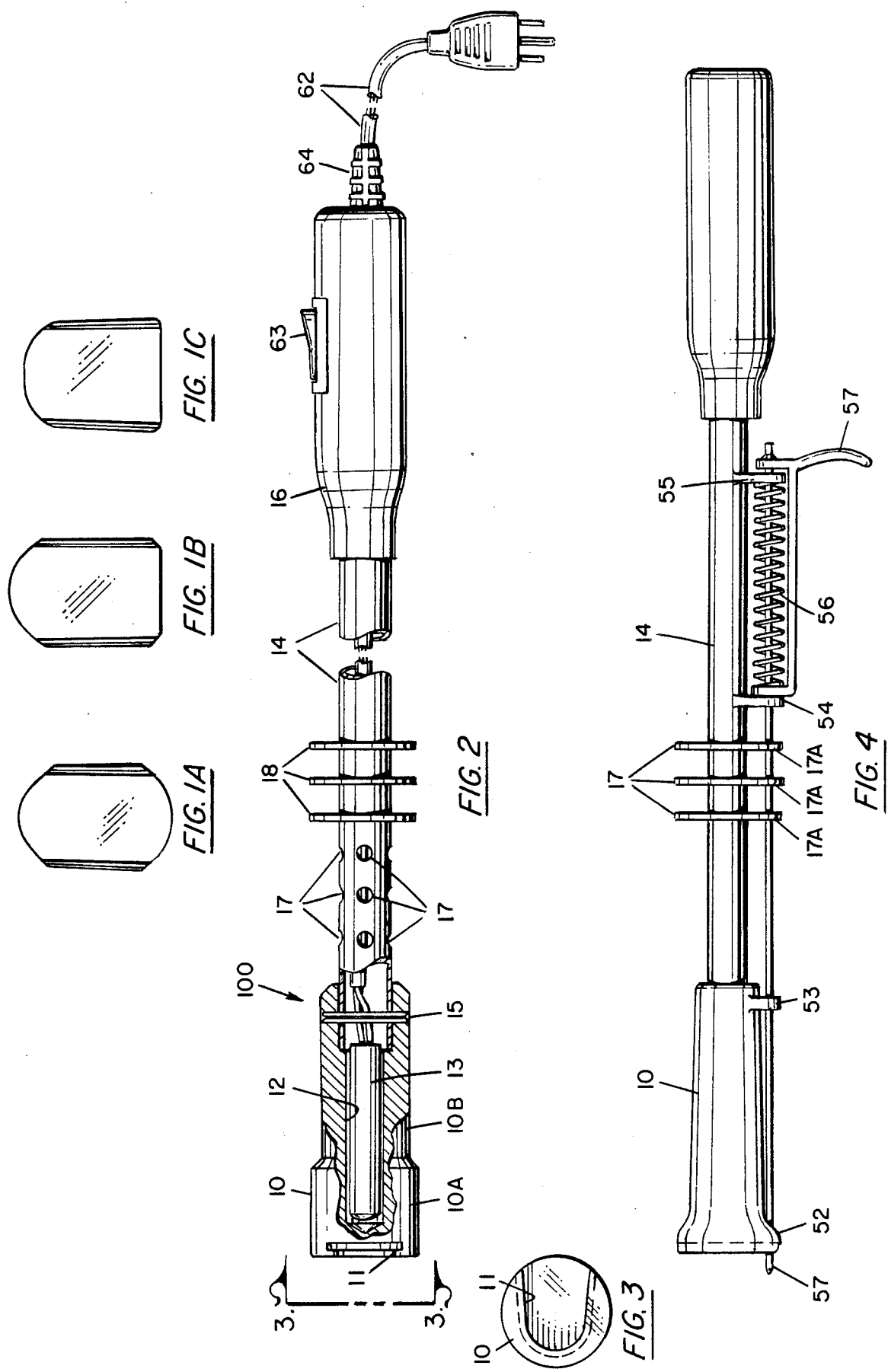

TOOL FOR REMOVING TABS AND BRACKETS FROM WINDSHIELDS

BACKGROUND

1. Field of the Invention

This invention is directed to a tool for removing the tabs and/or brackets used for mounting mirrors to windshields, in general, and to a tool which further permits single handed operation through the use of an electrically powered heater, in particular.

2. Prior Art

In many current and late model automobiles and similar vehicles, the inside, rear view mirror is attached to the windshield of the the vehicle rather than to the frame of the vehicle.

The attachment is, in many cases, made by means of a tab or base which is attached to the windshield proper. The tab is frequently made of metal, high impact plastic or similar material. The mirror is mounted to the tab in any conventional manner such as a swivel, ball and socket joint or the like. The tab or base is usually mounted to the windshield by means of a suitable glue. Typically, the glue is of the type referred to as Lock-tite mirror adhesive. This glue is, generally, not water soluble. However, the glue is, generally, heat sensitive wherein the glue melts with the application of the appropriate heat. Typically, the glue must attain a temperature of about 350°F. in order to become fluid. Thus, in order to remove the mirror bracket and/or tab, generation of heat in the order of 350°F. is required. In order to speed up the removal process a temperature of up to 750°F. may be used.

In the past, the normal procedure has been to use a propane or butane torch to apply heat and a suitable gripping tool such as a pair of pliers or the like to remove the tab. This procedure has been highly inadequate for a number of reasons. Obviously, it is very difficult to direct the heat from the propane or butane torch to precisely the location required. The application of heat in such a poorly controlled fashion leads to scorching of the tab, breaking of the glass, otherwise defacing the glass, possible fire damage to automobile interior and so forth.

Inasmuch as an additional tool such as pliers noted above, is required, a two handed operation is necessary. This also leads to the difficulty that the open flame torch may either impinge upon the hand of the tool holder or, conversely, it may impinge upon the tool. In either case, heat can be applied or transferred to the hand of the operator causing the obvious discomfort, if not injury.

Furthermore, with two hands being required, the task becomes quite cumbersome requiring either special tools and jigs for holding the windshield and/or the "tab remover apparatus" wherein the cost effectiveness of removing the tab is not very favorable.

Alternatively, it is sometimes required that two persons are necessary to hold the heat source in the appropriate location and apply pressure to the tab removing tool. Clearly, the cost effectiveness of this method is not very desirable either.

Likewise, in the past a procedure has been tried to remove the tabs by using a pry bar mechanism or the like. However, in the absence of application of heat, the glue or other adhesive remains intact. With this approach, it is more likely that the glass of the windshield will break before the tab is removed. Because of the large cost of a preformed glass windshield for an automobile, the breakage aspect is clearly undesirable and not very cost effective.

Consequently, a better, cheaper and more efficient method of removing the mirror tabs or brackets is highly desirable.

PRIOR ART STATEMENT

The most pertinent prior art known to applicant is:
U.S. Pat. No. 3,448,517; WINDSHIELD REMOVING TOOL; H. R. Cothery. This patent is directed to a tool having a blade for cutting through windshield glass and having a means for heating the blade to aid in the cutting process.

SUMMARY OF THE INSTANT INVENTION

This invention is directed to a tab removal tool for removing mirror mounting tabs from windshields. The tool includes a tab engaging barrel. The barrel includes a slot or recess which substantially conforms to the configuration of the tab wherein the tab can be held and, effectively, precluded from falling when detached from the windshield.

An electrical heater is connected to the barrel to apply temperatures which are appropriate to break down and deform the adhesive used in attaching the tab to the windshield. A suitable tube or connection is made to the barrel and heater to provide a handle or means for grasping the tool. In addition, appropriate venting devices and/or heat dissipating devices are provided to avoid injury to the user of the apparatus. An electrical connection is made to the heater to provide the power for generating the heat.

BRIEF DESCRIPTION OF THE DRAWINGS

FIGS. 1A, 1B and 1C are representative configurations of tabs which are adhered to windshields of vehicles for supporting mirror brackets or the like.

FIG. 2 is a side elevational view of the tool of the instant invention.

FIG. 3 is an end view of the barrel of the tool of the instant invention.

FIG. 4 is a side elevational view of another embodiment of the tool of the instant invention.

DESCRIPTION OF THE PREFERRED EMBODIMENTS

Referring now to FIGS. 1A, 1B and 1C there are three representative shapes or configurations of tabs which are affixed to the inside surface of windshields of vehicles. These tabs are used to mount the brackets which are attached to the rear surface of a rear view mirror in the vehicle. The tab shown in FIG. 1A is, in essence, an oblong or nearly rectagular tab with substantially rounded corners. This type of tab is frequently used in vehicles manufactured by the Ford Motor Company. A similar tab with less rounded bottom corners and shown in FIG. 1B is used by General Motors Corporation.

The third similar tab shown in FIG. 1C is used by the Chrysler Corporation. All three tabs are of about the same thickness. The third tab, as shown in FIG. 1C, is also taking the place of some of the tabs shown in FIG. 1B.

In general, the upper portion of the tab is, generally, arcuate while the bottom edge is substantially flat. Each of the tabs includes a bracket mounting means of suitable configuration. This bracket mounting means can be a swivel, a ball and socket arrangement or the like.

The tabs shown in FIGS. 1A, 1B and 1C are adhered to the inner surface of the windshield of an automobile of the types noted above. The tabs are mounted in place through the use of a suitable glue, such as Lock-tite mirror glue.

Referring now to FIG. 2, there is shown a side elevational view of the tab removal too of the instant invention.

In the preferred embodiment, the tool is, essentially, cylindrical so that the configuration is substantially identical when viewed from any position.

The tool 100 includes a barrel 10 which is substantially cylindrical in configuration. The barrel 10 may be fabricated of brass or any other material which transmits heat readily. Soft alloys such as aluminum, are generally excluded because they have a very low melting point.

In the embodiment shown in FIG. 2, the barrel 10 is a stepped configuration having two portions with different outer diameters. The end portion 10A is, generally, somewhat larger than the inner portion 10B. Of course, the segments 10A and 10B can be of the same outer diameter, if so desired. Typically, the end 10A is larger in order to accommodate the tab retaining slot 11 while inner portion 10B is smaller thereby reducing the overall dimensions of the barrel and, consequently, reducing the amount of material required. This has a cost saving effect. However, and perhaps more importantly, the smaller diameter of section 10B reduces the potential heat loss and power requirements of the tool.

As noted, the slot or recess 11 is formed in the end surface of barrel 10. The shape of the recess 11 is not critical but is, typically, an inverted U-shaped configuration so that it will readily engage and encompass tabs such as shown in FIGS. 1A, 1B and 1C.

The barrel 10 includes a central bore 12 therein. The bore 12 extends axially into the barrel from the end of segment 10B. However, the bore 12 does not, in the preferred embodiment, pass all the way through barrel 10 but stops short of the inner surface of recess 11 whereby heat can be produced at the rear surface of recess 11 as well as at the sides thereof.

The bore 12 is adapted to engage a heater element 13 which can be any suitable type of heater element such as a copper core or the like.

The heater element 13 can also include suitable receptacle (not shown) for receiving the core and which is connected to electrical wires or conductors 62 to receive electrical power for generating heat in the heater core 13. An electrical switch 63 can be included in the electrical lines for convenience.

The heater element is mounted at one end of a tube 14 which can be fabricated of stainless steel or the like. Tube 14 is, generally, a hollow tube which is adapted to receive the heater element 13. A suitable roll pin 15 or the like is used to prevent barrel 10 from turning or sliding in the tube 14. The same roll pin (or similar connector) can also be used to maintain barrel 10 in contact with tube 14 and heater 13. Of course, separate roll pins, set screws or the like can be used to effectuate this construction.

The stainless steel tube 14 is mounted in a suitable handle 16. The handle 16 can be fabricated of wood, plastic or any other suitable insulating device. The handle 16 is, preferably, insulating from both a thermal and an electrical point of view. This arrangement will prevent shocks and/or discomfort to the user of the device. The electrical conductors which are connected to heater 13 extend outwardly from the end of handle 16 in any conventional or convenient fashion. It is submitted that having the wires extend outwardly from the end of the tool permits a universal utilization of the tool without any preferred handling position or the like. Moreover, a suitable wire connector spiral or swivel arrangement 64 can be utilized for protection of the conductors.

A plurality of vent holes 17 are provided in the tube 14 adjacent to the barrel 10. The vent holes 17 permit heat to be released therethrough to prevent the barrel from becoming too hot.

In addition, one or more fins 18 in the form of disks or the like are mounted on a outer periphery of tube 14. In the embodiment shown, three disks or fins 18 are provided. However, any suitable or desirable number of fins can be provided. Again, fins 18 provide a heat dissipating device to diminish the heat which is transmitted along tube 14 toward the handle 16. The disks 18 can be fabricated of lock washers or other devices and, typically, are fabricated of aluminum.

Referring now to FIG. 3, there is shown an end view of the barrel 10. The recess 11 is shown to be an inverted U-shaped depression in the end surface of barrel 10. The recess 11 can be formed by molding, machining or any other suitable process.

Typically, the tool 100 is applied to the tabs shown in FIGS. 1A, 1B and/or 1C). That is, the slot 11 in barrel 10 is placed over the tab. The tool is plugged into any suitable electrical outlet and energized by operation of switch 63. In the embodiment described herein, the plug is engaged with any 110 volt outlet. When the heater element 12 is fully heated and the barrel 10 is applied to the tab to be removed, sufficient heat is generated so that the glue or adhesive is liquidified within 5 to 10 seconds and the tab is removed from the windshield. The tab is, usually, retained in the recess for ease in handling. The electrical power is removed and the barrel 10 is cooled.

Referring now to FIG. 4, there is shown an alternative embodiment of the instant invention. In this embodiment, components which are similar to components shown in FIG. 2 bear similar reference numbers. The remainder of the apparatus is substantially the same. However, in the embodiment shown in FIG. 4, a rod 51 passes through appropriate slots or apertures in bosses or extensions 52 and 53 which extend from or protrude from one side of barrel 10. The rod 57 passes backward and forward through these support members. The support members 52 and 53 operate to maintain the rod 51 in a relatively uniform position relative to the barrel 10.

In addition, the rod 51 can pass through apertures 17A in the disks or fins 17. Of course, if fins 17 are of small enough diameter, the rod 51 may pass beyond the edge thereof.

In addition, mounting brackets 54 and 55 can be mounted in a suitable fashion to the shaft or tube 14. The mounting brackets 54 and 55 also include apertures therethrough for receiving another end of rod 51.

A trigger mechanism 57 is mounted to the rod 51. Typically, the trigger 57 is mounted to rod 51 in a fixed arrangement so that movement of trigger 57 tends to move rod 51. The rod 51 and the trigger 57 can be joined together by welding, by appropriate lock washers and lock nuts or the like. A spring 56 is disposed between one end of trigger 56 and mounting bracket 55. Thus, when trigger 57 is pulled by the operator, spring 56 is compressed between the end of trigger 57 and support bracket 55. Conversely, when trigger 57 is released, the spring 56 forces the trigger and the associated rod 51 to the "home" position.

In the apparatus of this embodiment of the invention, the operator can place the barrel 10 over the tab on to be removed while pulling on trigger 57. When the tool has been sufficiently heated and placed in position long enough, the tab is released from the windshield inasmuch the glue has been liquified as before. In this case, the spring 56 exerts sufficient pressure on the trigger 57 and rod 51 so that the tool (along with the tab) is pushed away from the windshield by rod 51.

Thus, there is shown and described a unique design and concept of a tab tool. The particular configurations shown and described herein related to preferred configurations. While this description is directed to particular embodiments, it is understood that those skilled in the art may conceive modifications and/or variations to the specific embodiments shown and described herein. Any such modifications or variations which fall within the purview of this description are intended to be included herein as well. It is understood that the description herein is intended to be illustrative only and is not intended to be limitative. Rather, the scope of the invention described herein is limited only by the claims appended hereto.

I claim:

1. An apparatus for detaching items which are glued to a surface comprising,
    a heating element,
    a heat transfer element of generally cylindrical configuration connected to said heating element,
    one end of said heat transfer element comprising a relatively flat surface substantially normal to the length of said heat transfer element,
    said heat transfer element includes a recess in said relatively flat surface for receiving the items to be detached, and
    support means connected to support said heating element.
2. The apparatus recited in claim 1 wherein, said support means is formed of thermally insulating material.
3. The apparatus recited in claim 1 wherein, said heat transfer element includes a thermally conductive material.
4. The apparatus recited in claim 4 including, tube means connected between said support means and said heating element.
5. The apparatus recited in claim 4 including, fins extending from said tube means to conduct heat away from said tube means.
6. The apparatus recited in claim 4 wherein, said tube has a plurality of apertures passing through the surface thereof to provide a venting means.
7. The apparatus recited in claim 1 wherein, said heating element includes a thermally conductive core.
8. The apparatus recited in claim 7 wherein, said heating element includes electrical connections thereto.
9. The apparatus recited in claim 5 wherein, said fins are annular in configuration and extend radially outwardly from said tube means.
10. The apparatus recited in claim 1 including spring loaded release means mounted to said support means and adapted to force said apparatus means away from said surface.
11. The apparatus recited in claim 10 including, trigger means connected to said release means to selectively position said release means relative to said support means.
12. The apparatus recited in claim 1 wherein, said relatively flat surface is relatively larger than said heat transfer element.
13. The apparatus recited in claim 8 including, surface means connected to said electrical connections.

* * * * *